(12) United States Patent
Kunze et al.

(10) Patent No.: US 8,630,472 B2
(45) Date of Patent: Jan. 14, 2014

(54) INCREASED TEMPORAL RESOLUTION IN THE CASE OF CT IMAGES BY MEANS OF ITERATIVE VIEW RECONSTRUCTION WITH LIMITING CONDITIONS

(75) Inventors: Holger Kunze, Bubenreuth (DE); Harald Schöndube, Erlangen (DE); Karl Stierstorfer, Österreicher (DE)

(73) Assignee: Siemens Aktiengesellschaft, Munich (DE)

( * ) Notice: Subject to any disclaimer, the term of this patent is extended or adjusted under 35 U.S.C. 154(b) by 240 days.

(21) Appl. No.: 13/098,530

(22) Filed: May 2, 2011

(65) Prior Publication Data

US 2011/0268335 A1 Nov. 3, 2011

(30) Foreign Application Priority Data

May 3, 2010 (DE) .......................... 10 2010 019 016

(51) Int. Cl.
*G06K 9/00* (2006.01)
(52) U.S. Cl.
USPC .................. 382/131; 382/128; 378/4; 378/7; 378/8; 378/9; 378/11
(58) Field of Classification Search
USPC ............... 382/131, 128; 378/4, 7, 89, 11, 196
See application file for complete search history.

(56) References Cited

U.S. PATENT DOCUMENTS

| | | | | |
|---|---|---|---|---|
| 5,396,528 | A * | 3/1995 | Hu et al. ........................ | 378/14 |
| 7,381,959 | B2 * | 6/2008 | Manjeshwar et al. ... | 250/363.03 |
| 7,653,171 | B2 * | 1/2010 | Kunze et al. ...................... | 378/4 |
| 7,706,499 | B2 * | 4/2010 | Pack et al. ........................ | 378/9 |
| 7,916,828 | B1 * | 3/2011 | Khare et al. ...................... | 378/4 |
| 8,184,887 | B2 * | 5/2012 | Khare et al. ................... | 382/131 |
| 8,189,735 | B2 * | 5/2012 | Khare et al. ...................... | 378/4 |
| 2004/0066910 | A1 * | 4/2004 | De Villiers .................... | 378/901 |
| 2006/0269130 | A1 * | 11/2006 | Maroy et al. .................. | 382/173 |
| 2007/0093711 | A1 * | 4/2007 | Hoheisel et al. ............. | 600/407 |
| 2007/0165927 | A1 * | 7/2007 | Muradyan et al. ............ | 382/128 |
| 2008/0021304 | A1 * | 1/2008 | Stemmer ....................... | 600/410 |

(Continued)

FOREIGN PATENT DOCUMENTS

WO WO 2008147416 A1 12/2008

OTHER PUBLICATIONS

Heffernan, Patrick B.; Robb, Richard A.; , "Image Reconstruction from Incomplete Projection Data: Iterative Reconstruction-Reprojection Techniques," Biomedical Engineering, IEEE Transactions on , vol. BME-30, No. 12, pp. 838-841, Dec. 1983.*
Tim Nielsen, R.obert Manzkc, Thomas Koehler, ::Vlichael Grass, R.oland Proksa, "Iterative Cardiac Cone-Beam CT Reconstruction",Philips Research Laboratories, Medical Imaging 2004.*

(Continued)

*Primary Examiner* — Stephen R Koziol
*Assistant Examiner* — Shaghayegh Azima
(74) *Attorney, Agent, or Firm* — Harness, Dickey & Pierce, P.L.C.

(57) ABSTRACT

A method is disclosed for the reconstruction of image data of a moving object to be examined from measurement data, wherein the measurement data has previously been established in a relative rotational movement between a radiation source of a computed tomography system and the object to be examined. In at least one embodiment, first image data is reconstructed from an incomplete measurement data record by way of an iterative algorithm, wherein in the iterative reconstruction a dimension is used which contains probability information relating to pixel values of the image data to be reconstructed.

26 Claims, 3 Drawing Sheets

(56) References Cited

U.S. PATENT DOCUMENTS

| | | |
|---|---|---|
| 2008/0118020 A1 | 5/2008 | Basu |
| 2008/0129560 A1* | 6/2008 | Baraniuk et al. ............... 341/87 |
| 2008/0130826 A1* | 6/2008 | Harer et al. ..................... 378/8 |
| 2008/0177172 A1* | 7/2008 | John et al. ..................... 600/413 |
| 2008/0205737 A1* | 8/2008 | Kunze et al. .................. 382/131 |
| 2009/0057560 A1* | 3/2009 | Ray et al. .................. 250/363.04 |
| 2009/0074133 A1* | 3/2009 | Nielsen et al. ................. 378/19 |
| 2009/0123048 A1* | 5/2009 | Leroux et al. ................ 382/131 |
| 2009/0190814 A1 | 7/2009 | Bouman |
| 2010/0054394 A1* | 3/2010 | Thibault et al. .................. 378/8 |
| 2010/0054561 A1* | 3/2010 | Khare et al. .................. 382/131 |
| 2010/0303319 A1* | 12/2010 | Wang ........................... 382/131 |
| 2011/0044546 A1* | 2/2011 | Pan et al. ...................... 382/195 |
| 2011/0103662 A1* | 5/2011 | Chiang et al. ................. 382/130 |
| 2011/0123088 A1* | 5/2011 | Sebok ........................... 382/132 |
| 2011/0150305 A1* | 6/2011 | Zeng et al. ................... 382/131 |
| 2011/0150307 A1* | 6/2011 | Souza et al. .................. 382/131 |
| 2012/0019512 A1* | 1/2012 | Yang et al. .................... 345/419 |

OTHER PUBLICATIONS

Holger Kunze, Wolfgang Harer a, Karl Stierstorfer, "Iterative Extended Field of View Reconstruction", Siemens AG Medical Solutions, Medical Imaging 2007.*

Iterative Extended Field of View Reconstruction, Holger Kunze, Wolfgang Härer, Karl Stierstorfer, Siemens AG, Medical Solutions, Germany, Physics of Medical Imaging, Proc. of SPIE, vol. 6510 65105X-1; Magazine; 2007; DE.

Temporal resolution improvement using PICCS in MDCT cardiac imaging, Guang-Hong Chen, Jie Tang, Jiang Hsieh, Med. Phys. 36 (6); Magazine; 2009; US.

Iterative Rekonstruktion in der Medizinischen Bildverarbeitung, Holger Kunze, Technische Fakultät der Universitat Erlangen-Nürnberg; Others; 2007; DE.

German priority application No. DE 10 2010 019 016.0 filed on May 3, 2010 and not yet published.

German office action dated Feb. 16, 2011.

* cited by examiner

INCREASED TEMPORAL RESOLUTION IN THE CASE OF CT IMAGES BY MEANS OF ITERATIVE VIEW RECONSTRUCTION WITH LIMITING CONDITIONS

PRIORITY STATEMENT

The present application hereby claims priority under 35 U.S.C. §119 on German patent application number DE 10 2010 019 016.0 filed May 3, 2010, the entire contents of which are hereby incorporated herein by reference.

FIELD

At least one embodiment of the invention generally relates to a method for the reconstruction of CT images of a moving object to be examined from measurement data.

BACKGROUND

Tomographic imaging methods are characterized in that internal structures of an object to be examined can be investigated, without having to perform operative interventions thereupon. A possible type of tomographic image creation consists of a number of projections of the object to be examined from different angles. From these projections a two-dimensional cross-section or a three-dimensional volume image of the object to be examined can be calculated.

One example of such a tomographic imaging method is computed tomography. Methods for the scanning of an object to be examined with a CT system are generally known. Here, circular scanning, sequential circular scanning with advancement or spiral scans for example are used. Other types of scans too, which do not rely on circular movements are possible, thus for example scans with linear segments. With the aid of at least one X-ray source and at least one oppositely located detector, absorption data from the objects to be examined is recorded from different angles and these thus collected absorption data or projections apportioned to cross-sections through the object to be examined by means of corresponding reconstruction methods.

For the reconstruction of computed tomography images from X-ray CT data records of a computed tomography device (CT devices), that is from the established projections, so-called Filtered Back-Projection (FBP) is nowadays employed as the standard method. After the data capture a so-called "re-binning" step is generally performed, in which the data generated with the beam spreading out in a fan-like manner from the source is reordered in such a way that it exists in a form as if the detector were struck by X-ray beams approaching the detector in a parallel manner. The data is then transformed into the frequency range. A filtering takes place in the frequency range, and the filtered data is subsequently back-transformed. With the aid of the thus re-sorted and filtered data, a back-projection of the individual voxels within the volume of interest is then performed.

Iterative reconstruction methods have recently been developed. In such an iterative reconstruction method, a reconstruction of initial image data from the projection measurement data initially takes place. A convolution back-projection method can for example be used for this purpose. Synthetic projection data is then generated from this initial image data with a "projector", a projection operator, which is intended to map the measuring system as mathematically effectively as possible. The difference from the measurement signal is then back-projected with the operator adjointed to the projector and a residual image is thus reconstructed, with which the initial image is updated. The updated image data can in turn be used to generate new synthetic projection data in a next iteration step with the aid of the projection operator, from which again to form the difference to the measuring signals, and to calculate a new residual image, with which the image data of the current iteration stage is again improved, etc. With such a method it is possible to reconstruct image data which has relatively good image sharpness but at the same time little image noise.

One disadvantage of this generally known calculation method is that in the case of a moving object to be examined, or an at least partially moving object to be examined, motion blur can occur in the image, as during the period of a scanning process for the data which is required for an image, a locational displacement of the object to be examined or of a part of the object to be examined may exist, so that the basic data resulting in an image does not reflect all spatially identical situations of the object to be examined. This problem of motion blur arises in a particularly marked manner when performing cardio CT examinations of a patient, in which because of the movement of the heart a marked motion blur can arise in the cardiac area or for examinations in which relatively rapid changes in the object to be examined are to be measured.

SUMMARY

In at least one embodiment of the invention, a method is disclosed for the reconstruction of CT images of a moving object to be examined. A corresponding control and computation unit, a CT system, a computer program and a computer program product are further to be identified in other embodiments.

In at least one embodiment, a method is disclosed, and in other embodiments a control and computation unit, a CT system, a computer program and a computer program product are disclosed. Advantageous embodiments and developments are the subject matter of subsidiary claims.

In at least one embodiment of the inventive method for the reconstruction of image data of a moving object to be examined from measurement data, the measurement data has previously been established in the course of a relative rotational movement between a radiation source of a computed tomography system and the object to be examined. First image data is reconstructed from an incomplete measurement data record by means of an iterative algorithm. In the iterative reconstruction a dimension is here used which contains probability information relating to pixel values of the image data to be reconstructed.

The established measurement data comprises at least the incomplete measurement data record which is employed for the reconstruction of the first image data. In the case of computed tomography, 'incomplete' means that less measurement data than that from a semi-rotation is present. A semi-rotation corresponds to a projection angle range of 180° covered by the measurement in parallel beam geometry and 180° plus the fan opening angle in fan beam geometry. In addition to the incomplete measurement data record, it has been possible to establish a larger amount of measurement data, so that overall at least one complete measurement data record is present.

The calculation of the first image data takes place on the basis of an incomplete measurement data record. This has the advantage that the temporal resolution is hereby increased, which is important for the improvement of the image quality in the case of moving objects to be examined. This is because the time required for the capture of the incomplete measurement data record is less that that for the capture of a complete measurement data record.

The first image data can take the form of a two-dimensional cross-section or a three-dimensional volume image of the object to be examined.

An iterative algorithm is used for calculation of the first image data. There are many examples of this, such as the algebraic reconstruction technique (ART), the simultaneous algebraic reconstruction technique (SART), iterated filtered back-projection (IFBP), or statistical iterative view reconstruction techniques. The principle of an iterative reconstruction is that a CT image is calculated, which is used as the input image for the calculation of the iteration image of the next stage. It is here attempted, on a step-by-step basis, to adjust the iteration image as well as possible to the measurement data.

If an iterative algorithm were to be used unchanged on an incomplete measurement data record, the result image would thus be subject to artifacts as a result of this incompleteness. In order to prevent or at least reduce this, probability information relating to pixel values of the image data to be reconstructed is employed. It is hereby possible to enforce particular statistical behavior of the pixel value of the first image data. The probability information can in particular specify how probable—relative to all or some pixel values—the incidence of the particular pixel values is, or how probable—relative to all or some pixels—the incidence of a certain pixel value of the respective pixel relative to a specific quantity of other pixels is.

It is particularly advantageous to use the dimension as a limiting condition in the iterative reconstruction. Such a limiting condition must be met by the result image of the iterative reconstruction.

In one embodiment of the invention the probability information refers only to a partial quantity of the pixels of the image data to be reconstructed. This partial quantity can, for example, derive from a querying of the pixel values. The possibility thus exists of not applying the probability information to pixels which have specific prescribed pixel values. In one application of this principle, for example, only those pixels can be considered for the probability information which have a pixel or attenuation value of less than 1000 HU, due to the assumption that attenuation values higher than this represent bones, the high temporal resolution representation of which is not an objective of the underlying application.

In a development of at least one embodiment of the invention second image data is reconstructed from a complete measurement data record of the measurement data, and the second image data is used for determining of the probability information. An image with a temporal resolution inferior to that of the first image data is thus present, which serves to enable probability information to be obtained.

In particular a histogram of the pixel values of the second image data can be determined from the second image data, and a probability density distribution of the pixel values of the second image data from the histogram. For the histogram, the frequency with which each pixel value is contained in the second image data is counted. From this it is accordingly possible to calculate a probability density distribution of all or some pixel values. For example the probability information can represent the logarithmized probability density values.

The histogram can relate to the entire image. Alternatively it is also possible to determine one or more histograms, which in each case refer only to one specific image region of the second image data.

It is advantageous to smooth the histogram or histograms prior to calculation of the probability information.

In a development of at least one embodiment the invention the probability information contains percentile specifications referring to a pixel value relative to the pixel values in the particular environment. Alternatively, in examining the environment of a pixel, the entire image can also be considered, so that the probability information contains percentile specifications relating to a pixel value with reference to the pixel values in the remaining image.

It is particularly advantageous if according to the percentile specifications a pixel value must not be smaller than a percentile threshold value, wherein the percentile threshold value is a pixel value which is at least attained or exceeded by a specific percentage of the pixel values in the particular environment or in the remaining image. The particular examination of small pixel values is advantageous insofar as the limited angle artifacts have an effect particularly in this value range. If a pixel value were smaller than the percentile threshold value, it is for example possible to induce it to be equal to the percentile threshold value or another value.

In the iterative reconstruction the probability information is preferably employed as a regularization term in a cost function to be minimized. This makes it possible to adapt existing cost functions to at least one embodiment of the inventive method.

The first image data can be output as the result image. As an alternative to this, it is possible for the further improvement of the result image, to mix the first image data with image data based on a complete measurement data record. For example mixing with the second image data is possible. The mixing corresponds to a weighted or unweighted pixel-wise addition of two or more images. It preferably takes place depending upon movement information of the object to be examined. This makes it possible to use the first image data with the higher temporal resolution exclusively or mainly for image regions in which movement of the object to be examined is present. In the case of cardio CT this is for example the coronary arteries.

In a development of at least one embodiment of the invention in the case of iterative reconstruction the objective of the smallest possible total variation of the image data to be reconstructed is used as a limiting condition. This can be employed as a limiting condition in addition to the probability information. In the case of a one-dimensional function the total variation is defined as the integral over the value of the derivative. It represents a dimension for local fluctuations within the image. The use of the total variation is a measure which is known per se in the view reconstruction from underscanned data.

At least one embodiment of the inventive control and computation unit serves to reconstruct image data of an object to be examined from measurement data of a CT system. It comprises a program memory for the storage of program code, wherein—where appropriate among other contents—program code is contained which is suitable to perform a method of the aforementioned kind or to effect or control such performance. At least one embodiment the inventive CT system comprises such a control and computation unit. It can further contain other components, which for example are required for the capture of measurement data.

At least one embodiment of the inventive computer program has program code, which is suitable to perform the method of the kind described above, if the computer program is executed on a computer.

At least one embodiment of the inventive computer program product comprises a program code stored on a computer-readable data medium, which is suitable to perform the method of the kind described above, if the computer program is executed on a computer.

BRIEF DESCRIPTION OF THE DRAWINGS

The invention is explained in greater detail below on the basis of an example embodiment. Wherein.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
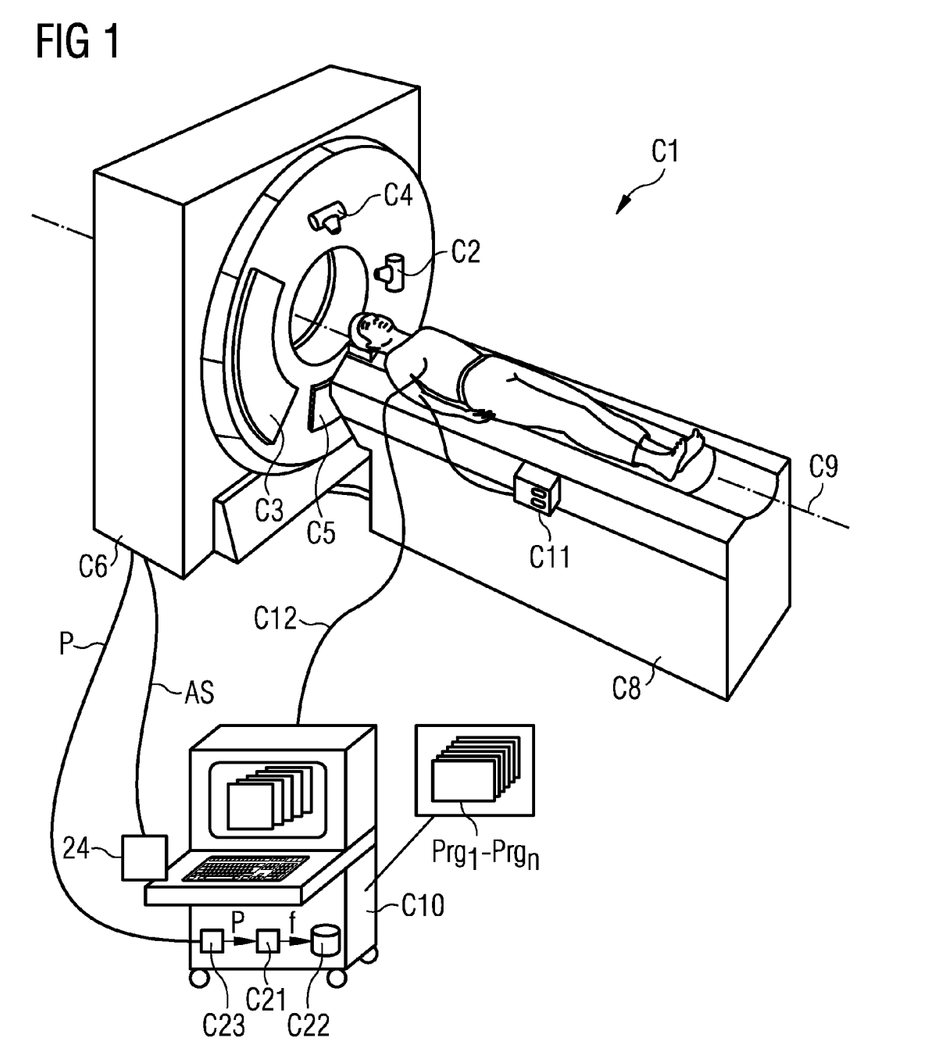
FIG. 1: shows a first schematic representation of an example embodiment of a computed tomography system with a view reconstruction component.

FIG. 1 initially represents, in schematic form, a first computed tomography system C1 with a view reconstruction device C21. It here takes the form of a CT device of the so-called third generation, to which an embodiment of the invention is, however not restricted. In the gantry housing C6 is located a closed gantry, which is not shown here, on which are arranged a first X-ray tube C2 with an oppositely located detector C3. Optionally, a second X-ray tube C4 with an oppositely located detector C5 is arranged in the CT system shown here, so that by way of the tube unit/detector combination additionally available here, a higher temporal resolution can be achieved, or with the use of different X-ray energy spectrums in the tube unit/detector systems, "Dual-Energy" investigations can also be performed.

The CT system C1 further has a patient couch C8, upon which during the investigation a patient can be advanced along a system axis C9, also designated the z axis, into the measuring field, wherein the scanning itself can take place both as a pure circular scan without advancement of the patient exclusively in the area of investigation of interest. The movement of the patient couch C8 relative to the gantry is effected by way of suitable motorization. During this movement the X-ray source C2 or C4 respectively rotates around the patient. The detector C3 or C5 respectively travels in parallel opposite the X-ray source C2 or C4, in order to capture projection measurement data, which is then used for the reconstruction of cross-sections. As an alternative to a sequential scan, in which the patient is advanced gradually between the individual scans through the area of investigation, the possibility of a spiral scan also of course exists, in which the patient is continuously advanced along the system axis C9 through the area of investigation between X-ray tube C2 or C4 and detector C3 or C5 during the rotational scanning with the X-rays. As a result of the movement of the patient along the axis C9 and the simultaneous rotation of the X-ray source C2 or C4 respectively, a helical path is yielded in a spiral scan for the X-ray source C2 or C4 respectively relative to the patient during the measurement. This path can also be achieved by the gantry being moved along the axis C9 with the patient immobile. It is further possible to move the patient continuously and periodically between two points.

The CT system 10 is controlled by a control and computation unit C10 with computer program code $Prg_1$ to $Prg_n$ which is present in a memory. It should be pointed out that these computer program codes $Prg_1$ to $Prg_n$ can of course also be contained on an external storage medium and loaded into the control and computation unit C10 as required.

Acquisition control signals AS can be transferred from the control and computation unit C10 via a control interface 24, in order to activate the CT system C1 according to certain measurement protocols. The acquisition control signals AS here relate, for example, to the X-ray tubes C2 and C4, wherein stipulations relating to their output and the timing of their activation and deactivation can be made, and the gantry, wherein stipulations relating to its rotation speed can be made, and the advancement of the table.

As the control and computation unit C10 has an input console, measurement parameters can be entered by a user or operator of the CT device C1, which then control the data capture in the form of acquisition control signals AS. Information about measurement parameters currently being used can be displayed on the screen of the control and computation unit C10; in addition, further information of relevance to the operator can also be displayed.

The projection measurement data p or raw data acquired from detector C3 or C5 respectively is transferred to the control and computation unit C10 via a raw data interface C23. This raw data p is then, if appropriate after a suitable initial preparation, further processed in a view reconstruction component C21. In this example embodiment the view reconstruction component C21 is realized in the control and computation unit C10 in the form of software on a processor, for example in the form of one or more of the computer program codes $Prg_1$ to $Prg_n$. As already explained with reference to control of the measuring procedure, it is the case with regard to the view reconstruction that the computer program codes $Prg_1$ to $Prg_n$ are also contained on an external storage medium and loaded into the control and computation unit C10 as required. It is further possible that the control of the measuring procedure and the view reconstruction are performed by different computation units.

The image data reconstructed by the view reconstruction component C21 is then deposited in a memory C22 of the control and computation unit C10 and/or output on the screen of the control and computation unit C10 in the customary manner. It can also be fed into a network connected to the computed tomography system C1 via an interface not shown in FIG. 1, for example a radiological information system (RIS), and stored in a mass storage unit accessible there or output as images.

The control and computation unit C10 can additionally perform the function of an EKG, wherein a line C12 is used to derive the EKG potential between the patient and control and computation unit C10. In addition the CT system C1 shown in FIG. 1 also has a contract medium injector C11, via which in addition contrast medium can be injected into the blood stream of the patient, so that for example the vessels of the patient's body, in particular the cardiac chambers of the beating heart, can more effectively be represented. In addition the possibility hereby also exists to perform perfusion measurements, for which the proposed method is likewise suitable.

Figure 2:
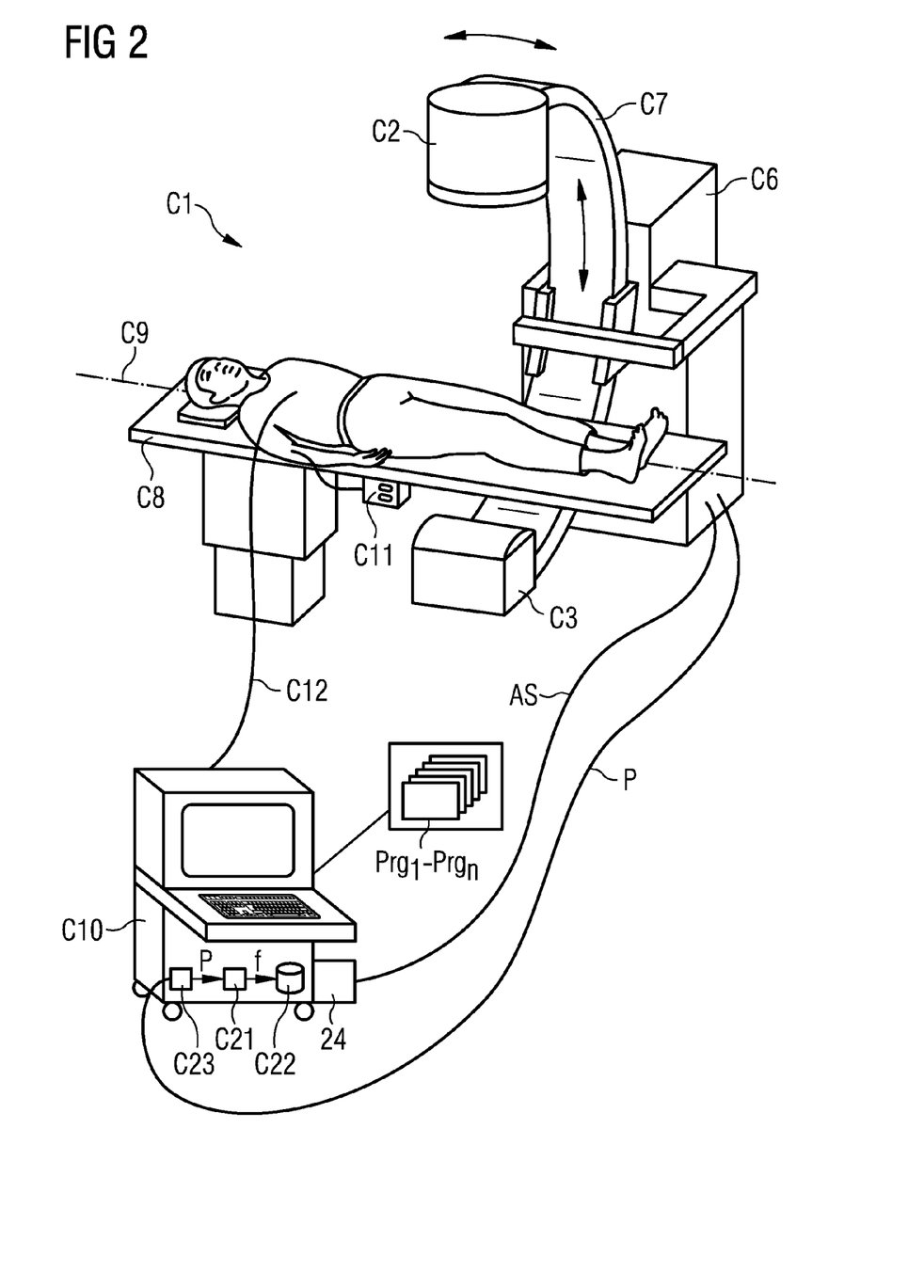
FIG. 2: shows a second schematic representation of an example embodiment of a computed tomography system with a view reconstruction component.

FIG. 2 shows a C-arm system, in which in contrast to the CT system in FIG. 1 the housing C6 carries the C-arm C7, on which on the one hand the X-ray tube C2 and on the other the oppositely located detector C3 are fixed. For scanning purposes, the C-arm C7 is likewise pivoted about a system axis C9, so that scanning from a multiplicity of scanning angles can take place and corresponding projection data can be established from a multiplicity of projection angles. The C-arm system C1 from FIG. 2 has, like the CT system from FIG. 1, a control and computation unit C10 of the kind described with reference to FIG. 1.

Embodiments of The invention can be applied in both of the systems shown in FIGS. 1 and 2. In principle it can also be used for other CT systems, for example for CT systems with a detector forming a complete ring.

Insofar as body parts of a patient are to be scanned which can be rendered immobile or still, no notable problems with motion artifacts arise for the recording of the projections and the subsequent view reconstruction. This is on the other hand critical in the case of moving objects to be examined. There follows a consideration of the situation where a CT image of a moving object to be examined is to take place.

Figure 3:
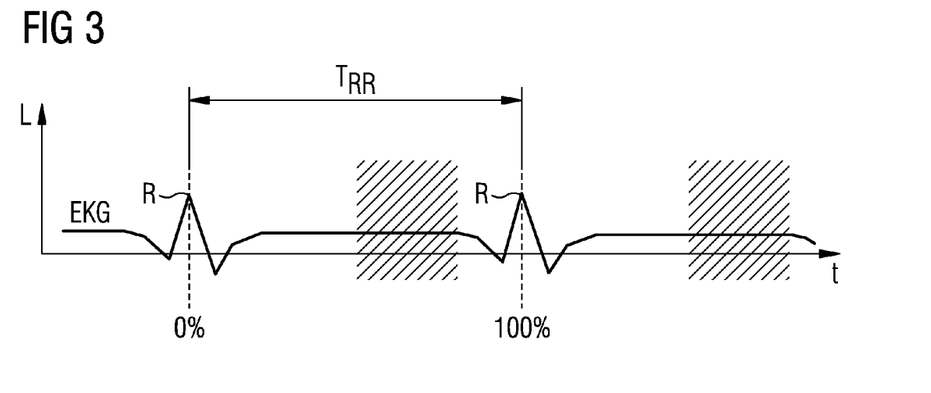
FIG. 3: shows the motion cycle of the human heart.

An example of a periodically moving object to be examined is the human heart. An embodiment of the invention is explained in greater detail below on the basis of the cardio CT, that is a CT image of the beating heart. It is, of course not restricted to this application. It is known that the human heart essentially performs a periodic movement. The periodic movement here comprises an alternating sequence of a resting/diastolic phase and a motion/systole. The resting phase has a duration of generally between 500 and 800 ms, the systole a duration of 200 to 250 ms. This is evident from FIG. 3, in which the level L of the EKG signal of a patient indicated by EKG is applied over the period t. The EKG signal illustrates the periodic movement of the heart of the patient, wherein the beginning of a cardiac cycle is in each case determined by a R-wave R and the duration of the respective cardiac cycle by the RR interval $T_{RR}$, that is the distance of the R-wave R initiating the respective cardiac cycle from the R-wave R initiating the following cardiac cycle. A cardiac phase starts upon a R-wave R at 0% and ends upon the next R-wave R at 100%. A conversion between the dimension of the time and the cardiac phase is possible at any time; for this purpose it is possible to use the EKG data, from which it can be concluded at any point in time, which cardiac phase is currently present. The resting phase of the heart, that is the phase of minimum heart movement, is indicated in each case in hatched form.

Besides the requirements in terms of the quality of CT images also applying to immobile objects to be examined, in the case of cardiac images the objective exists to achieve a high temporal resolution of the images. The temporal resolution is here inversely proportional to the period of time which is necessary for the capture of the projections. The more time which elapses during the data capture, the more the heart moves during this period of measurement. This movement leads to unwelcome motion artifacts in the CT images. The meaningfulness of the CT image is hereby drastically reduced.

For the CT view reconstructions during a measurement in parallel beam geometry a data interval, that is a series of successive projections must be available, wherein each projection corresponds to a measurement at a particular projection angle, which corresponds to at least a semi-rotation of the X-ray source around the object to be examined, that is a projection angle range of 180°. In the case of a fan beam geometry, the projection angle range must amount to 180° plus the fan opening angle. Both cases are combined in the following under the designation "data of a semi-rotation" or "complete data record". This minimum data interval is necessary, in order to be able to reconstruct each pixel in the measuring field. In the center of rotation a projection angle range of 180° is sufficient in the case of fan beam geometry too. The best possible temporal resolution in a thus reconstructed CT image thus amounts in the vicinity of the center of rotation to precisely half the rotational period of the CT device. In the case of a rotational speed of the gantry of 0.5 seconds per revolution, a maximum temporal resolution of 0.25 seconds can thus be achieved.

A widespread approach to the reduction of motion artifacts is to increase the rotational speed of the gantry. However this imposes exacting and in some cases insoluble requirements on the mechanical elements of the gantry and is for this reason highly cost-intensive.

A further hardware-based approach for increasing temporal resolution is the use of a second tube/detector system, which is arranged offset by 90° relative to the first system. A so-called Dual Source System is involved here. Both the systems which are offset at 90° record measurement data at the same time, so that a projection angle coverage of 180° is already attained after a gantry rotation of 90°, which corresponds to a doubling of the temporal resolution.

A further approach, which is employed primarily in cardiac imaging, is to split the data acquisition into several sections of in each case less than 180°, which in total amount to a projection angle range of 180° and which in each case depict the same movement status of the heart, though for successive heartbeats. This involves so-called multi-segment reconstruction.

The publication

G. Chen, J. Tang, J. Hsieh: Temporal resolution improvement using PICCS in MDCT cardiac imaging, Med. Phys. 36 (6), June 2009, p. 2130-2135, the entire contents of which are hereby incorporated herein by reference, recently described an algorithm, with the aid of which under certain preconditions CT images can be reconstructed from a restricted projection angle range, whereby the temporal resolution is increased.

There follows a description of another method for increasing the temporal resolution, which is based on an iterative reconstruction. An incomplete data record is used for this iterative reconstruction. As a limiting condition of the iterative algorithm, probability information about the CT values to be achieved is fed into the CT image to be calculated.

Figure 4:
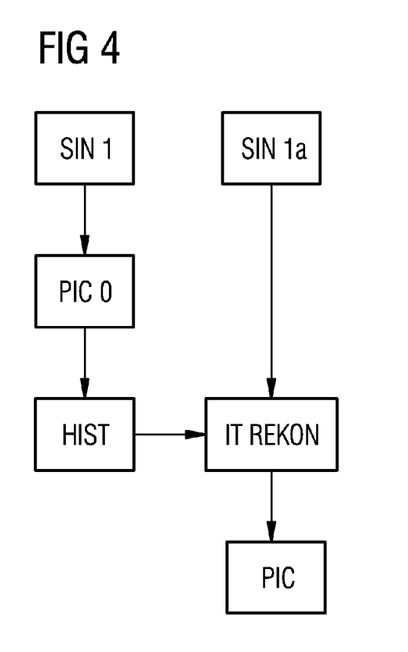
FIG. 4: shows a flow chart.

A first embodiment of such a method is explained on the basis of the flow chart in FIG. 4. The data is initially established, for which the sinogram SIN1 is available. The sinogram represents a two-dimensional space for each detector line, which on the one hand is spanned by the projection angle, that is the angularity of the X-ray source relative to the object to be examined, and on the other hand by the fan angle within the X-ray beam, that is to say by the position of the detector pixel in the channel direction. The sinogram space thus represents the domain of the measurement data, while the image space represents that of the image data.

An image PIC0 reconstructed from the complete data record SIN1. Here, for example, a classic FBP (Filtered Back-projection) method can be employed. As a result of the movement of the object to be examined the image PIC0 has motion artifacts. The image PIC0 serves solely as the interim result.

In the next step, a histogram HIST of this image PIC0 is determined from the image PIC0. The probability density distribution of the CT values within of the image PIC0 is to be taken from the histogram HIST. An incomplete data record SIN1$a$ is subsequently used, in order to calculate the image PIC from this by means of an iterative algorithm IT REKON. The incomplete data record SIN1$a$ represents a partial quantity of the complete data record SIN1. The temporal resolution of the image PIC is directly dependent on the angle area, over which the data record SIN1$a$ extends. If, for example, the angle area of the incomplete data record SIN1$a$ is 120°, then the temporal resolution of the image PIC amounts to 120°/180°=⅔ of the temporal resolution of the image PIC0.

A conventional iterative reconstruction based on the incomplete data record SIN1$a$ would not lead to a satisfactory result, as the resultant image exhibits so-called "limited angle artifacts" due to the incomplete nature of the data record. In order to prevent this, the iterative reconstruction IT REKON is performed using the histogram HIST as a regularization or limiting condition. The use of this prior knowledge in the form of the probability information results in a highly effective reduction of limited angle artifacts.

The determining of a histogram of a CT image and its subsequent use in an iterative view reconstruction is explained in the publications:

H. Kunze, W. Harer, K. Stierstorfer: Iterative Extended Field of View Reconstruction, Medical Imaging 2007: Physics of Medical Imaging, Proc. of SPIE Vol. 6510, 65105X-1 to 65105X-12

US 2008/0205737 A1 of Aug. 28, 2008 the entire contents of each of which are hereby incorporated herein by reference and included in full in the present description.

These publications are based on the problem of the exceeding of the measuring field. In this case there is thus incomplete data relating to an object to be examined which extends across the Scanning Field of View (SFOV). The reasons for this are for example, that the object to be examined is larger than the SFOV or that the object to be examined is positioned in such away that parts ultimately lie outside the SFOV, in the latter case for example in order to reduce the X-ray exposure to which sensitive organs are subject. In this case there are thus parts of the objects to be examined, from which CT images are to be reconstructed, for which however, projections from an angle area of at least 180° have not been obtained. As the measured projections are incomplete or, expressed graphically, "truncated", this problem is also designated as truncated projection(s).

The publications included are thus not concerned with the problem of CT images of moving objects to be examined and the associated desire for higher temporal resolution, but rather with the exceeding of the measuring field. In the case of both sets of problems, however, an incomplete data record is to be used for the image reconstruction.

There follows a more detailed explanation of the use of the histograms HIST for the iterative reconstruction IT REKON.

A modification of conventional iterative reconstruction methods takes place through the introduction of A-priori information about the statistics on material-specific attenuation values, that is the CT values, of the region to be reconstructed of the objects to be examined based on a probability function. This is formed from a logarithmic probability distribution of the material-specific attenuation values. This extension is embedded in an iterative reconstruction method, in the case of an algebraic iterative reconstruction for example by adding a limiting condition term as a regularization function to the cost function, which is to be minimized within the framework of the iterative reconstruction.

Algebraic iterative reconstruction algorithms minimize the quadratic errors between the measured projections Y and calculated projections. If a calculated image X is involved, the calculated projections are obtained by applying a projection operator A to the image X. A takes the form of an operator which maps the measurement process in the best possible manner. The cost function K of the algebraic reconstruction can be described as follows:

$$K = \|Y - AX\|^2 \quad (1)$$

It is thus attempted to match the calculated image X as closely as possible to the measurement data Y.

The application of iterative algorithms—such as the algebraic reconstruction technique (ART), the simultaneous algebraic reconstruction technique (SART) or iterated filtered back-projection (IFBP)—to an incomplete data record leads, as already described, to unsatisfactory solutions, as a result of the incomplete nature of the data record Y without the introduction of limiting conditions. Limited angle artifacts occur in the result image.

In order nevertheless to find a satisfactory solution, a regularization of the cost function K is employed. This means that the cost function K is expanded by a second term, which contains a regulation term R(X)

$$K = \|Y - AX\|^2 + \beta \cdot R(X) \quad (2)$$

The regulation term R(X) penalizes improbable values within of the image X. $\beta$ is a regulation parameter, which is to create a balance between the difference term and the regulation term.

It should be emphasized that embodiments of the invention are not limited to the use of algebraic iterative reconstruction algorithms. The cost functions of other iterative reconstruction methods, such as for example of statistical reconstruction can be modified in an analogous manner. In order to keep R(X) as simple as possible, it should be assumed that the pixel values of the reconstructed image are uncorrelated. R(X) can accordingly be written as $$R(X) = -\log\left(\prod_i pdf(x_i)\right) = -\sum_i \log(pdf(x_i)) \quad (3)$$

$pdf(x_i)$ being the probability density of the pixel value of the i-th pixel $x_i$. The cost function augmented by R(x) according to formula (3) can now be minimized for example by means of the gradient descent method, in order to calculate the image PIC.

The determining of the underlying probability density function takes place in that the histogram HIST of the image PIC0 is established and the probability density function calculated from this. The image PIC0 thus serves to provide information about the distribution of CT values which should obtain within the image PIC. It is not disadvantageous here that the image PIC0 contains motion artifacts.

The limited angle artifacts have an effect such that in the respective image many of the low CT values are too small, that is to say they are shifted erroneously downwards, and many of the high CT values are too large, that is they are shifted erroneously upwards. It is thus sensible to use the probability distribution of the CT values as a stipulation, as it is hereby possible to enforce a situation where these excessively low or excessively high values occur only in limited numbers, which corresponds to a reduction of the limited angle artifacts.

The probability distribution calculated from the histogram HIST is in general subject to interference from severe noise, which leads to a function course which has many local minima and maxima. As, however, part of the cost function K is formed form this function, which for example is to be minimized by means of gradient descent algorithms, these many local minima and maxima disrupt and impair the minimization process. It is thus advantageous to smooth the histogram HIST, in order to reduce the number of minima and maxima. With regard to a possible type of smoothing, attention is drawn to the publications cited above.

As the initial image of the iterative algorithm IT REKON it is possible to use a reconstructed image based on the incomplete data record SIN1a. In order to speed up the convergence of the iterative algorithm IT REKON, it is advantageous to employ the image PIC0 as the initial image.

The reconstructed image PIC is largely free of artifacts. This applies both to the motion artifacts, as these are prevented, in that the incomplete data record SIN1a has been used as the basis for the view reconstruction. This further also applies to the limited angle artifacts, as these have been avoided by the prior knowledge about the distribution of the CT values from the image PIC0 being incorporated into the iterative reconstruction.

It is thus possible to output the image PIC as the result image. Alternatively the image PIC can be mixed with the image PIC0 for further quality improvement, wherein the image PIC is only or mainly used for those pixels in which motion is present. To this end it is first necessary to decide which image regions are affected by movement of the object to be examined. This can, for example, take place in that two CT images, which represent different points in time, are compared with each other. This can, for example, take the form of the image PIC0 and a different image based on a complete measurement data record, or the images PIC0 and PIC. This comparison makes available the requisite movement information. For regions with little movement, the pixel values of the image PIC0 can be in incorporated into the result image, while for regions with movement, the pixel values of the image PIC are incorporated into the result image. The calculation of the result image can be obtained by means of a weighted sum of the images PIC0 and PIC, wherein the weighting factors depend on the movement information.

Use of the movement information is also then advantageous if the image PIC0 is employed as the initial image for the iterative reconstruction IT REKON, in that the image PIC0 weighted with the movement information is used as the initial image for the iterative reconstruction IR REKON. The iterative algorithm IR REKON can further be modified in such a way that only in such areas of the image, in which according to the movement information movement is present, is an updating performed in the corresponding iteration steps, while the unmoving image regions remain unchanged in the course of the iteration.

In the previous description, histogram HIST related to the entire image PIC0. Even better results are obtained if the image PIC0 is divided into individual regions, and histograms created individually for these regions. These regions are preferably those which are affected by the movement of the objects to be examined. In that the histograms are more precisely matched to the region to be reconstructed, the statistical statements arrived at hereform are of higher quality, which results in an improved image quality. A further possibility is to create a histogram individually for each pixel value, which in each case relates to a particular environment around the pixel being considered.

Instead of calculation of the image PIC0 and of the histogram HIST yielded therefrom for the determining of probability information as a suitable limiting condition for the iterative reconstruction IT REKON, the following alternative procedure may be adopted: Instead of statements obtained from the histogram HIST, percentiles which relate to the current iteration image are employed as probability information. This takes place in that each pixel is examined for the current iteration image. The pixel values in the environment of this pixel are analyzed. If the pixel value of the pixel being examined lies below a specific percentile threshold value of the pixels in its environment, then the particular pixel value is set to this percentile threshold value. The percentile threshold value is calculated as a pixel value, at or above which a specific percentage of pixel values in the environment being examined lie. For example in the case of the 25% percentile, the percentile threshold value would be that value above which 75% of all pixel values in the environment being examined lie. This process is followed with each individual pixel of the current iteration image.

As an alternative to the calculation of the percentile threshold value from the current iteration image as described, this can also be calculated from the image PIC0.

Instead of the environment around the pixel concerned, it is also possible to use the entire image for the calculation of the percentile threshold value. Alternatively it is further possible to use a particular subarea of the image for the calculation of the percentile threshold value; for the application of the percentile threshold values the image can also be divided into "subimages", within which movement is performed.

This comparison of the pixel values with the percentile threshold value and the exchange of the pixel values with the percentile threshold value to be performed if applicable, can be employed as a limiting condition within the context of the iterative view reconstruction IT REKON. Examining the pixels with low pixel values makes sense, because as already explained, the limited angle artifacts result in the shifting of small pixel values to even smaller values. If by means of a limiting condition their shift to larger values is induced, then at the same time there is an automatic reduction in the effect whereby the limited angle artifacts bring about the shifting of large pixel values to even larger pixel values.

If this procedure is followed, no calculation of the histogram HIST is necessary. In this case the image PIC0 is not necessarily required as an interim result. If however, as described above, the image PIC is not to be output as the result image, but a mixture of the image PIC with the image PIC0, or the image PIC0 is to be employed as initial image for the iterative reconstruction IT REKON, then the calculation of the image PIC0 must nevertheless take place.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

In the foregoing the invention has been described for an example embodiment. It should be understood that numerous amendments and modifications are possible, without being outside the context of the invention.

What is claimed is:

1. A method for the reconstruction of image data of a moving object to be examined from measurement data, wherein the measurement data is established by a relative rotational movement between a radiation source of a computed tomography system and the object to be examined, the method comprising:
reconstructing first image data from an incomplete measurement data record by way of an iterative algorithm;
reconstructing second image data from a complete measurement data record of the measurement data; and
outputting final image data based on at least the first image data, wherein
the reconstructing first image data includes using a dimension which contains probability information relating to pixel values of the image data to be reconstructed, and
the second image data is used to determine the probability information.

2. The method as claimed in claim 1, wherein the dimension is employed as a limiting condition for the iterative reconstruction.

3. The method as claimed in claim 1, wherein the incomplete measurement data record is a partial quantity of the complete measurement data record.

4. The method as claimed in claim 1, wherein the probability information relates only to a partial quantity of the pixels of the image data to be reconstructed.

5. The method as claimed in claim 1, further comprising:
determining a histogram of the pixel values from the second image data; and
determining a probability density distribution of the pixel values from the determined histogram.

6. The method as claimed in claim 1, further comprising:
determining a multiplicity of histograms for a multiplicity of image regions of the second image data.

7. The method as claimed in claim 5, wherein the histogram is smoothed prior to the calculation of the probability information.

8. The method as claimed in claim 1, wherein the probability information contains percentile specifications relating to a pixel value of a desired pixel with reference to the pixel values contained in a particular environment, the particular environment being a region surrounding the desired pixel.

9. The method as claimed in claim 1, wherein the probability information contains percentile specifications relating to a pixel value of a desired pixel with reference to the pixel values in the remaining image.

10. The method as claimed in claim 8, wherein, according to the percentile specifications a pixel value is not smaller than a percentile threshold value, and wherein the percentile threshold value is a pixel value which is exceeded by a specific percentage of the pixel values in the particular environment.

11. The method as claimed in claim 1, wherein, in the iterative reconstruction, the probability information is employed as a regularization term in a cost function which is to be minimized.

12. The method as claimed in claim 1, wherein the outputting includes mixing the first image data with the second image data to obtain the final image data.

13. The method as claimed in claim 12, wherein the mixing takes place depending on the movement information of the objects to be examined.

14. The method as claimed in claim 1, wherein, for the iterative reconstruction, the objective of a smallest possible total variation of the image data to be reconstructed is used as a limiting condition.

15. A control and computation unit for the reconstruction of image data of an object to be examined from measurement data of a CT system, comprising:
a program memory, program code being stored in the program memory, the program code, when executed, enabling the control and computation unit to perform the method according to claim 1.

16. A CT system comprising the control and computation unit as claimed in claim 15.

17. A non-transitory computer readable medium including program segments for, when executed on a computer device, causing the computer device to implement the method of claim 1.

18. A computer program product, comprising program code of a computer programs stored on a non-transitory computer-readable data medium, to perform the method as claimed in claim 1 when the computer program is executed on a computer.

19. The method as claimed in claim 2, wherein the incomplete measurement data record is a partial quantity of the complete measurement data record.

20. The method as claimed in claim 2, wherein the probability information relates only to a partial quantity of the pixels of the image data to be reconstructed.

21. The method as claimed in claim 2, further comprising:
determining a histogram of the pixel values from the second image data; and
determining a probability density distribution of the pixel values from the determined histogram.

22. The method as claimed in claim 5, further comprising:
determining a multiplicity of histograms for a multiplicity of image regions of the second image data.

23. The method as claimed in claim 6, wherein the histograms are smoothed prior to the calculation of the probability information.

24. The method as claimed in claim 9, wherein, according to the percentile specifications, a pixel value is not smaller than a percentile threshold value, and wherein the percentile threshold value is a pixel value which is exceeded by a specific percentage of the pixel values in the remaining image.

25. The method as claimed in claim 1, wherein the incomplete measurement data record corresponds to an amount of data obtained from a semi-rotation of the radiation source with respect to the object being examined.

26. The method as claimed in claim 25, wherein the semi-rotation corresponds to one of a projection angle range of less than 180° for parallel beam geometry and a projection angle range of less than a sum of 180° and a fan opening angle for fan beam geometry.

* * * * *